United States Patent [19]

Elisha

[11] 4,351,434

[45] Sep. 28, 1982

[54] DISPOSAL OF NEEDLES

[76] Inventor: Benjamin Elisha, 5 Mooltan Ave., East St. Kilda, 3183, Victoria, Australia

[21] Appl. No.: 116,768

[22] Filed: Jan. 30, 1980

[30] Foreign Application Priority Data

Jan. 31, 1979 [AU] Australia .................... PD7508

[51] Int. Cl.³ .............. A61M 5/32; B02C 19/12; B21D 7/00
[52] U.S. Cl. .................................. 206/366; 206/63.5
[58] Field of Search ................. 206/365, 366, 63.5

[56] References Cited

U.S. PATENT DOCUMENTS

| | | | |
|---|---|---|---|
| 1,213,289 | 1/1917 | Soloff | 206/63.5 |
| 2,413,858 | 1/1947 | Borgeat | 206/43 |
| 2,553,232 | 5/1951 | Beyer | 206/63.5 |
| 2,985,285 | 5/1961 | Riddle | 206/17.5 |
| 3,381,814 | 5/1968 | Benfield | 206/63.5 |
| 3,876,067 | 4/1975 | Schwarz | 206/366 |

FOREIGN PATENT DOCUMENTS

| | | |
|---|---|---|
| 459754 | 3/1973 | Australia . |
| 464114 | 4/1973 | Australia . |
| 53192 | 6/1980 | Australia . |
| 2740335 | 3/1979 | Fed. Rep. of Germany ..... 206/63.5 |
| WO79/00239 | 5/1979 | PCT Int'l Appl. . |
| 587356 | 4/1947 | United Kingdom . |
| 685660 | 1/1953 | United Kingdom . |
| 821070 | 9/1959 | United Kingdom . |
| 1244137 | 8/1971 | United Kingdom . |
| 1396464 | 6/1975 | United Kingdom . |

Primary Examiner—William T. Dixson, Jr.
Attorney, Agent, or Firm—Scully, Scott, Murphy & Presser

[57] ABSTRACT

The present invention provides a container for receiving and containing hypodermic needles, the container having an opening through which a disposable needle having a needle shank and a hub can be passed while mounted to a syringe but which, on retraction of the syringe, can engage with the hub to draw the needle off the syringe.

7 Claims, 5 Drawing Figures

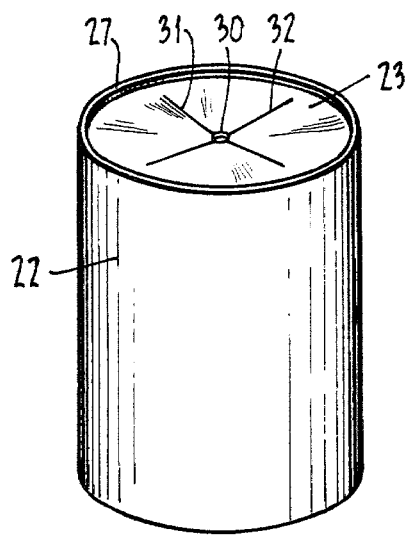
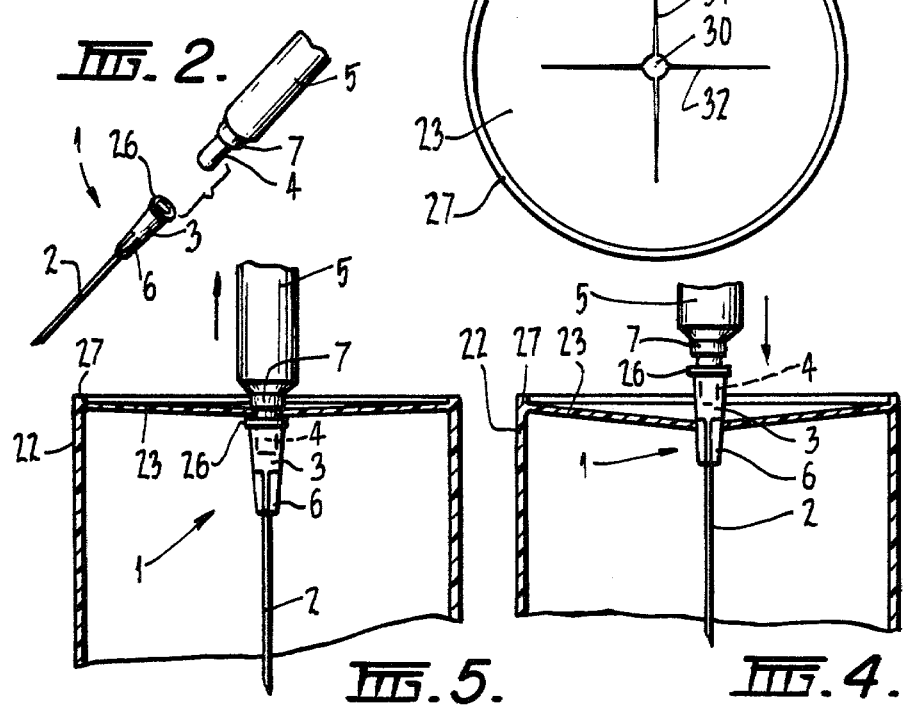
FIG. 1.
FIG. 2.
FIG. 3.
FIG. 4.
FIG. 5.

DISPOSAL OF NEEDLES

FIELD OF THE INVENTION

This invention relates to the disposal of hypodermic needles.

BACKGROUND TO THE INVENTION

It is well known that hypodermic needles can transmit diseases such as serum hepatitis and for this reason it has become common medical practice to use a needle once only and thereafter to discard it.

However, the discarded needles, which may carry a disease, are a hazard.

Because discarded needles are sharp they, if placed within a plastic rubbish bag, will often project from the bag to form a hazard for medical personnel, the public and garbage disposal workers.

Thus, it is highly desirable that discarded needles be collected in a container.

I believe that it is also desirable that to place a needle in a container it should be unnecessary to touch the needle as if the needle is not touched the risk of spreading disease is reduced.

SUMMARY OF THE INVENTION

Accordingly, the present invention provides a container for receiving and containing hypodermic needles, the container having an opening through which a disposable needle having a needle shank and a hub can be passed while mounted to a syringe but which, on retraction of the syringe, can engage with the hub to draw the needle off the syringe.

PREFERRED ASPECTS OF THE INVENTION

The container is preferably made non-openable except by being physically broken.

Hypodermic syringes of the type known as Luer lock require that the hub be rotated on the syringe before it can be released therefrom and to deal with these it is preferred that the opening has a portion adapted to engage the hub of the needle and restrict it against rotation so that a Luer lock syringe can be rotated. Thereafter, the needle can be removed from the syringe.

Hypodermic syringes of the type known as Luer slip do not require that the hub be rotated before the needle can be removed and a suitable form of said opening is that it should widen as the hub is passed therethrough and thereafter contract behind the hub so that when the syringe is retracted the needle will tend to be pulled off the syringe. In this instance, the preferred form of the opening is that it is a slit in a resilient member; in an alternative, two intersecting slits are used.

The internal dimensions of the container are important in that the needles, which enter point first, might, if shaken, turn around within the container and come to project out of the opening. Accordingly, it is preferred that the container is dimensioned so that this cannot occur. In this last respect, the largest dimension of the container transverse to the direction in which the needle enters should be smaller than the smallest needle likely to be inserted, a suitable dimension is about 1 inch.

Containers in accordance with this invention may be formed by blow moulding plastics material.

A specific construction of containers in accordance with this invention will now be described with the aid of the accompanying drawings.

BRIEF DESCRIPTION OF THE VIEWS OF THE DRAWINGS

FIG. 1 is a perspective view of the other one of the containers,

FIG. 2 is a view of a needle mounted on the end of a syringe,

FIG. 3 is a top plan view of the container of FIG. 1, and

FIGS. 4 and 5 are fragmentary cross-sectional views showing the container of FIG. 1 in use.

DETAILED DESCRIPTION

In FIG. 2 is shown a hypodermic needle 1 comprised of a needle shank 2 and a hub 3. The hub 3 is of non-circular cross-section at 6. The hub is mounted on a spigot 4 of a syringe 5 having a shoulder 7.

The container shown in FIG. 1 is shown having a top wall 23 with two intersecting slots or lines of weakness 31 and 32 extending from a hole 30, the top wall 23 is resilient, the top wall 23 is also slightly concave and has an upstanding peripheral ridge 27.

The hole 30 is preferably of axial length substantially the same as the thickness of the top 23 of the container and that length is preferably not substantially greater than the minimum distance between the end 26 of the hub 3 and the syringe 5 or any shoulder, such as 7, on the syringe which will not enter the hole 30. In general, that length should be not greater than about 1.4 mm.

The slots 32 are preferably four in number and are spaced about 90° apart. When this last is the case it is found that the non-circular cross-section at 6 of the hub 3 can locate partly in the hole 30 and partly in the slots 32 and if the syringe is of the Luer lock type it can be rotated to separate the hub 3 from the syringe. Thereafter the hub 3 may be pushed through the hole 30 with the end of the syringe.

The hole 30 is preferably sized to suit the spigot 4 and in general it is preferred that the hole 30 is about 4 mm in diameter.

The material defining the hole 30 both in respect of the upper and lower ends is preferably substantially normal to the axis of the hole immediately adjacent the hole.

The container of FIG. 1 has been found by me to be useful with all types of syringes known to me. In particular, it works with Luer lock and Luer slip types, types with and without a shoulder 7, types with eccentric and concentric nozzle and even those of eccentric nozzle where the barrel terminates other than at the base of the nozzle.

The presence of the concavity in the top wall 23 and the ridge 27 make it unlikely that a needle will accidently slip off the top wall 23.

The container of FIG. 1 may be narrower than the length of the needle 1. Preferred dimensions are about 8.5 cm high and 6.5 cm wide.

Since the top walls 23 might become disease carriers, a removable cover may be provided.

The containers of this invention permit the rapid and simple disposal of needles which will encourage busy doctors and nurses to use the containers. Further, the containers are themselves disposable when desired.

The claims form part of the disclosure of this specification.

Modifications and adaptations may be made to the above described without departing from the spirit and scope of this invention which includes every novel feature and combination of features disclosed herein.

I claim:

1. A container for receiving and containing hypodermic needles, the container having an opening therein; comprising a generally circular hole and a plurality of slits or lines of weakness which will break into slits radiating from the opening; and wherein the axial length of the hole is substantially the same as the thickness of said wall whereby a disposable needle having a needle shank and a hub can be passed while mounted to a spigot on a syringe having a body so that said wall locates between said hub and said body and so that on retraction of the syringe engagement of the side of said wall within the container with said hub will move the needle off the syringe.

2. A container as claimed in claim 1, wherein the container is non-openable except by being physically broken.

3. A container as claimed in claim 1 or claim 2, wherein the opening has a portion adapted to engage with the hub of the needle of a syringe and restrict it against rotation.

4. A container as claimed in claim 3, wherein the opening comprises two or more intersecting slits or two or more lines of weakness are provided in the container along which, in use, a break will occur to define two or more intersecting slits.

5. A container as claimed in claim 1, wherein the largest internal dimension of the container transverse to the direction in which the needle enters in use is smaller than the smallest needle likely to be inserted.

6. A container as claimed in claim 1, wherein the container has a top, a bottom and side wall means joining the top and bottom all integral with one another.

7. A container as claimed in claim 1 and having an upstanding ridge at least substantially entirely surrounding said opening.

* * * * *